US00PP09340P

United States Patent [19]

Wilhelm et al.

[11] Patent Number: Plant 9,340

[45] Date of Patent: Oct. 24, 1995

[54] RASPBERRY PLANT CV. 'ISABEL'

[75] Inventors: Stephen Wilhelm, Alamo; Carlos D. Fear, Aptos, both of Calif.

[73] Assignee: Sweetbriar Development, Inc., Watsonville, Calif.

[21] Appl. No.: 350,941

[22] Filed: Dec. 7, 1994

[51] Int. Cl.[6] ..... A01H 5/00

[52] U.S. Cl. ..... Plt./46.2

[58] Field of Search ..... Plt./46.2

*Primary Examiner*—James R. Feyrer

*Attorney, Agent, or Firm*—Synnestvedt & Lechner

[57] ABSTRACT

A new and distinct variety of red raspberry plant named 'Isabel', which is particularly characterized and distinguished by its consistently large size fruit of excellent flavor and color and its high yielding capacity on both primocane and floricane crops.

3 Drawing Sheets

BACKGROUND AND SUMMARY OF THE INVENTION

This invention relates to a new and distinct cultivar of raspberry plant that has been given the variety name or denomination 'Isabel'. The new cultivar was developed from hybridization of the selection B36.7 (an unpatented variety) as the seed parent with the selection C44.1 (an unpatented variety) as the pollen parent. The parents were crossed by Stephen Wilhelm in 1987, whereafter fruit and seed were collected to produce seedlings for field planting in Watsonville, Calif., in 1988. The new variety was selected from these seedlings by Carlos Fear in 1989 for their large, attractive fruit. Since its selection the 'Isabel' plants have been evaluated in several noncommercial experimental plantings in Watsonville, Calif. The 'Isabel' variety has been asexually propagated by in vitro shoot tip culture, root sucker division and root cuttings, and has been shown to maintain the desired and distinguishing characteristics after propagation over several generations.

The 'Isabel' raspberry plant produces a relatively early primocane crop which begins in July and continues until late October. The floricane crop begins in early May and continues until about mid-July. Both the primocane and floricane yields are high relative to other comparable varieties. The fruit of the 'Isabel' raspberry plant is large and remains consistently so throughout its harvest period. The fruit has a very pleasant flavor and darkens only slightly after harvest.

DETAILED DESCRIPTION OF THE PLANT

Figure 1:
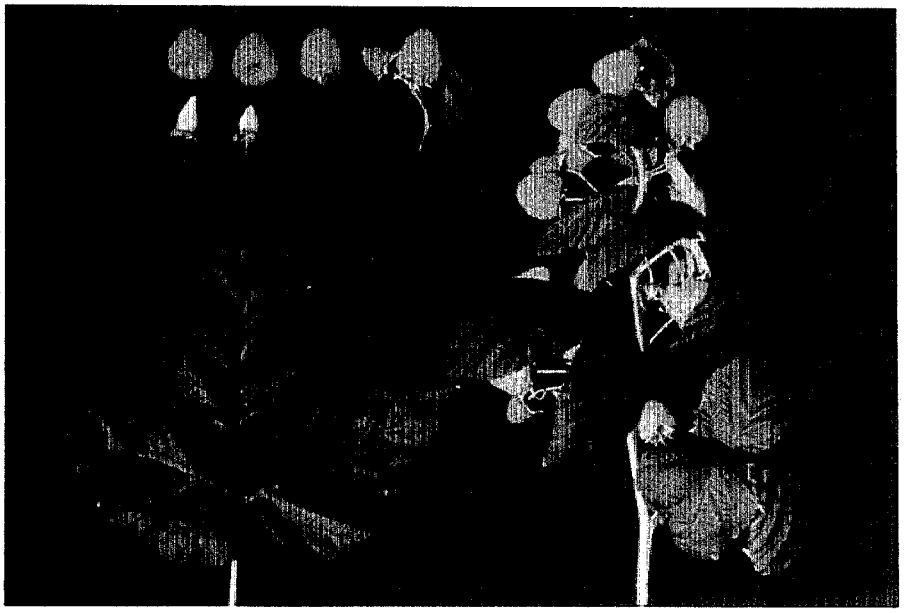
FIG. 1 is a photograph of an 'Isabel' floricane mature leaf and fruiting shoot, showing various stages of fruit development.
Figure 2:
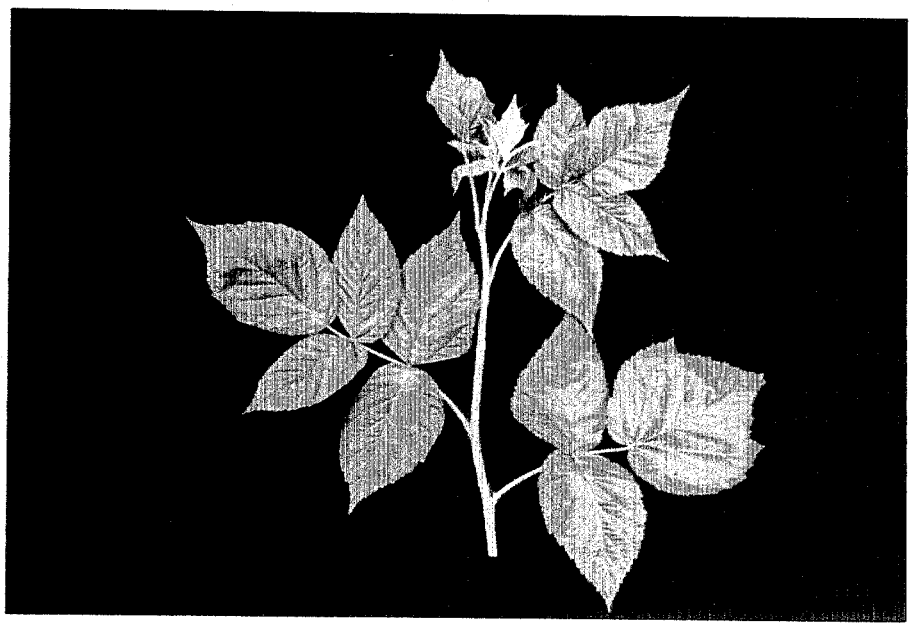
FIG. 2 is a photograph of an 'Isabel' primocane shoot.

Throughout this specification, color names beginning with a small letter signify that the name of the color, as used in common speech, is aptly descriptive. Color names beginning with a capital letter designate color values based on The R.H.S. Colour Chart published by The Royal Horticultural Society of London, England.

The following description is a detailed description of the 'Isabel' raspberry cultivar and the fruit produced thereby, as grown in Watsonville, Calif. between 1991 and 1994, and is believed to apply to plants of the 'Isabel' variety grown in similar conditions of soil and climate elsewhere.

The 'Isabel' fruit size is large and does not decline as much as most varieties throughout the fruiting cycle. Fruit color darkens only slightly after harvest. The fruit of the 'Isabel' plant is average or moderate in its ease of separation and of moderate firmness at harvest. Post harvest fruit rot resistance is intermediate in comparison with many selections and varieties.

The 'Isabel' variety has moderate susceptibility to late leaf rust and powdery mildew. Resistance to root rots is unknown and cold tolerance of the new variety has not been established.

The new variety is particularly characterized and distinguished from other cultivars by it high yields on both primocanes and floricanes. It is further distinguished by its large, bright red fruit of excellent flavor, which maintains its large size through the harvest season. The 'Isabel' variety also fruits earlier in the spring than most other cultivars.

'Isabel' is distinguished from its pollen parent, selection C44.1, by fruiting earlier in the spring, having larger fruit size, and yielding more fruit. The new variety is distinguished from its seed parent by having a higher yielding capacity with more uniform fruit shape.

Tables 1 and 2 below present morphological information about the new 'Isabel' raspberry cultivar.

TABLE 1

PLANT CHARACTERISTICS OF 'Isabel'

| | |
|---|---|
| General | |
| Plant size: | medium |
| Growth habit: | erect |
| Density of foliage: | medium |
| Productivity: | very productive |
| Self fruitfulness: | self fruitful |
| Primocane fruiting: | |
| percent of cane length flowering as primocane: | about 40–50% |
| percent of total yield from primocane crop: | about 45–50% |
| Suckering tendency: | medium |
| Utility of fruit: | various |
| Canes | |
| Primocanes | |

TABLE 1-continued

| PLANT CHARACTERISTICS OF 'Isabel' | |
|---|---|
| Number of fruiting laterals/cane: | many/about 15–20 |
| Number of canes/crown: | few/about 4–7 |
| Young shoot pigmentation: | weak |
| Length: | about 69–84" |
| Diameter (end of 1st year): | |
| cane base: | about 0.40–0.78" |
| central 1/3 of cane: | about 0.31–0.62" |
| Depressions in cross section: | absent |
| Prickles: | |
| pigmentation: | pigmented |
| density on young shoots: | medium |
| attitude of tip: | horizontal |
| size: | medium |
| texture: | rigid |
| presence and distribution on petioles: | uniformly distributed |
| Pubescence on canes: | absent to very slight |
| Internodal distance (at central 1/3 of cane): | about 1.5–3.0" (1.9" mean) |
| Lenticels: | not visible |
| Floricanes | |
| Length: | about 48–72" |
| Number lateral branches per cane: | about 6–16 |
| Number nodes/lateral (at mid cane): | about 11–15 |
| Number of flowers/node (at 4th node from apex on a mid cane lateral): | about 2–5 |
| Leaves | |
| Arrangement: | compound |
| Relief between veins: | medium |
| Leaflet number: | 3–5, usually 5 |
| Terminal leaflet: | |
| length: | about 4.9–6.5" |
| width: | about 3.7–5.7" |
| shape: | ovate |
| tip: | acuminate |
| base: | cordate |
| margin: | doubly serrate |
| Lateral leaflets (basal pair): | |
| overlap: | touching to slight overlap |
| orientation: | opposite |
| shape: | oblique |
| tip: | acuminate |
| base: | oblique |
| margin: | doubly serrate |
| length: | about 4.3–5.8" |
| width: | about 3.2–4.0" |
| Rachis length between terminal leaflet and adjacent lateral leaflets: | about 0.75–2.1" |
| Color: | |
| face: | Green 137A–137B |
| underside: | Green 191B |
| Petiole: | |
| length: | about 4.5–7.3" |
| pigmentation of upper surface: | often pigmented |
| pigmentation of underside: | unpigmented |
| Stipule orientation: | erect |
| Flowers | |
| Flowering period: | |
| primocane: | early June to late October |
| floricane: | early April to mid-June |

TABLE 1-continued

| PLANT CHARACTERISTICS OF 'Isabel' | |
|---|---|
| Petal: | |
| color: | White 155B–155D |
| length: | about 0.22–0.28" |
| width: | about 0.12–0.16" |
| number: | 5 |
| arrangement: | free |
| Pedicel coloration: | weak |

TABLE 2

| FRUIT CHARACTERIZATION OF 'Isabel' | |
|---|---|
| Fruit | |
| Harvest season: | |
| primocane: | early; begins mid- to late July; ends late October; uniform ripening over a long period (about 90–100 days) |
| floricane: | very early; begins early to mid-May; ends mid-July; ripens uniformly over a long period (about 60 days) |
| Color: | |
| immature: | Red 39A |
| maturing: | Red 47A–47B, glossy |
| mature: | Red 53B |
| Dimensions: | |
| weight: | |
| primocane harvest: | about 3.7–5.4 g (4.5 g mean) |
| floricane harvest: | about 3.4–5.1 g (4.4 g mean) |
| length (primocane): | about 0.66–0.94" |
| width (primocane): | about 0.63–0.81" |
| Soluble solids (%): | about 8.5–9.1% (8.8% mean) |
| Titratable acidity (% as citric acid): | about 1.5% |
| Seeds: weight: | about 1.1–1.6 mg (1.3 mg mean) |
| Number drupelets/fruit: | about 76–118 (101 mean) |

Figure 3:
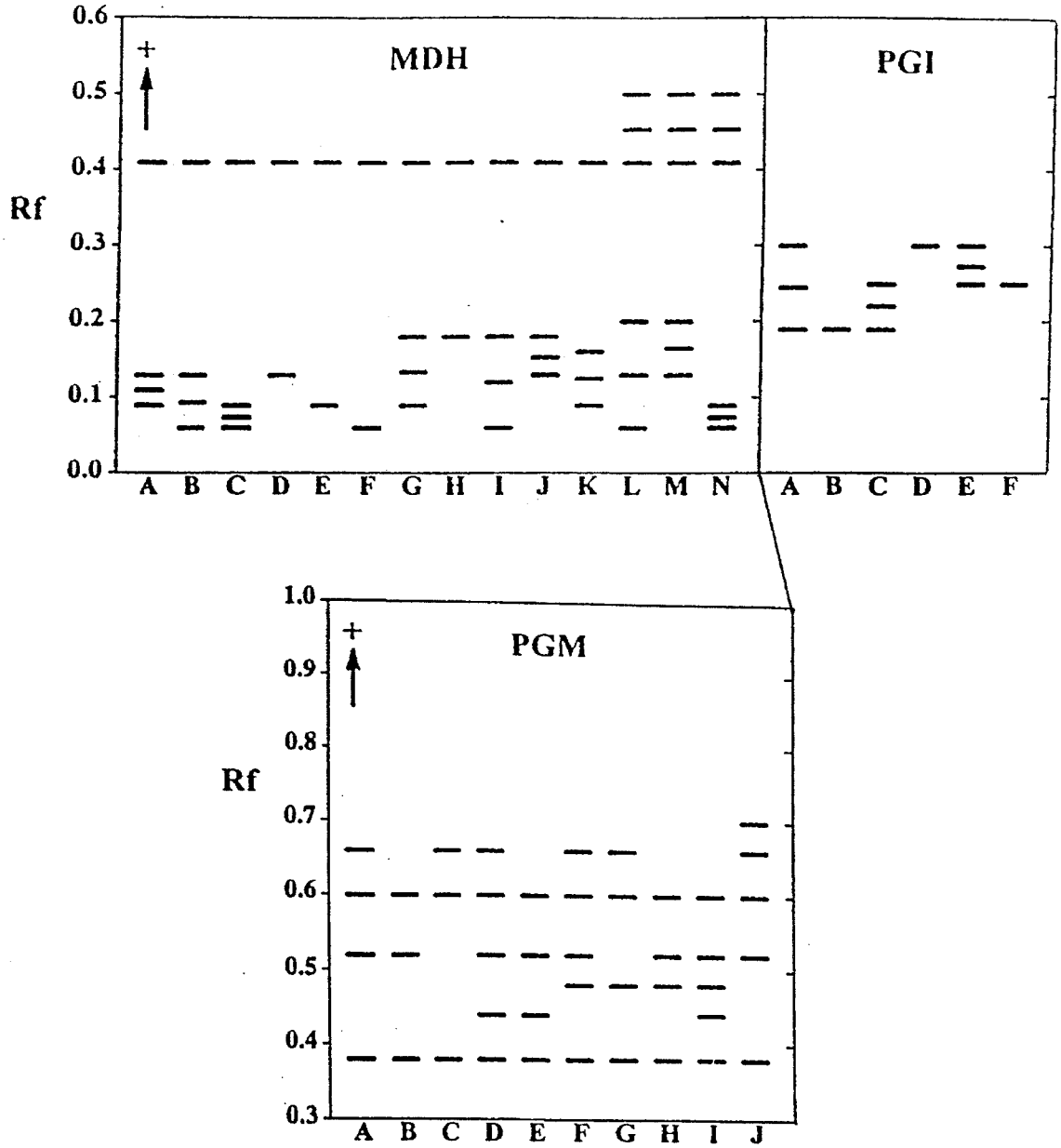
FIG. 3 is an interpretative drawing showing the cultivar banding patterns for the enzymes, MDH (malate dehydrogenase), PGI (phosphoglucoisomerase) and PGM (phosphoglucomutase).

In addition to the foregoing morphological description, and to provide further means for identifying the new variety and distinguishing it from some other somewhat similar and/or related raspberry varieties, the new 'Isabel' variety has been analyzed to obtain an indication of its genetic makeup. Specifically, leaves of the 'Isabel', 'Hollins' (U.S. Plant Pat. No. 8,027), 'Summit' (unpatented), 'Wilhelm' (U.S. patent applied for), 'Sweetbriar' (U.S. Plant Pat. No. 4,486), and 'Joe Mello' (U.S. Plant Pat. No. 6,493) varieties were electrophoretically analyzed, the patterns designated and procedures utilized being per those described by J. C. Cousineau and D. J. Donnelly, "Use of Isoenzyme Analysis to Characterize Raspberry Cultivars and Detect Cultivar Mislabeling," *HortScience,* vol 27 (9):1023–1025 (1992). The results of the electrophoresis analysis are presented in Table 3 below, the letters representing the cultivar banding patterns for each enzyme as shown in FIG. 3, taken from the above article.

TABLE 3

ISOZYME BANDING PATTERNS OF 'Isabel' COMPARED WITH 'Hollins', 'Summit', 'Wilhelm', 'Sweetbriar' AND 'Joe Mello'

| Cultivar | Isozyme and Pattern | | |
|---|---|---|---|
| | PGI | MDH | PGM |
| 'Isabel' | A | E | C |
| 'Hollins' | D | E | D |
| 'Summit' | A | C | B |
| 'Wilhelm' | D | A | C |
| 'Sweetbriar' | D | D | A |

TABLE 3-continued

ISOZYME BANDING PATTERNS OF 'Isabel' COMPARED WITH 'Hollins', 'Summit', 'Wilhelm', 'Sweetbriar' AND 'Joe Mello'

| Cultivar | Isozyme and Pattern | | |
|---|---|---|---|
| | PGI | MDH | PGM |
| 'Joe Mello' | D | E | C |

We claim:

1. A new and distinct variety of raspberry plant named 'Isabel', as herein illustrated and described.

* * * * *

UNITED STATES PATENT AND TRADEMARK OFFICE

CERTIFICATE OF CORRECTION

PATENT NO. : Plant 9,340

DATED : October 24, 1995

INVENTOR(S) : Stephen Wilhelm and Carlos D. Fear

It is certified that error appears in the above-indentified patent and that said Letters Patent is hereby corrected as shown below:

Column 4, line 24; "100" should read --110--.

Signed and Sealed this

Twenty-first Day of January, 1997

*Attest:*

Bruce Lehman

BRUCE LEHMAN

*Attesting Officer*

*Commissioner of Patents and Trademarks*